(12) United States Patent
Chan

(10) Patent No.: US 7,398,575 B2
(45) Date of Patent: Jul. 15, 2008

(54) ELECTRIC TOOTHBRUSH HAVING A FLEXIBLE DRIVE SHAFT

(75) Inventor: John Geoffrey Chan, Maineville, OH (US)

(73) Assignee: Church & Dwight Co., Inc., Princeton, NJ (US)

( * ) Notice: Subject to any disclaimer, the term of this patent is extended or adjusted under 35 U.S.C. 154(b) by 465 days.

(21) Appl. No.: 11/052,593

(22) Filed: Feb. 7, 2005

(65) Prior Publication Data
US 2005/0177962 A1    Aug. 18, 2005

Related U.S. Application Data

(60) Provisional application No. 60/545,325, filed on Feb. 17, 2004.

(51) Int. Cl.
A61C 17/34 (2006.01)
A46B 13/02 (2006.01)

(52) U.S. Cl. .......................... 15/22.1; 15/22.2
(58) Field of Classification Search ............. 15/22.1, 15/22.2
See application file for complete search history.

(56) References Cited

U.S. PATENT DOCUMENTS

| | | | |
|---|---|---|---|
| 3,757,375 A * | 9/1973 | Strom | 15/104.33 |
| 4,081,876 A | 4/1978 | Pugh | |
| 4,845,795 A | 7/1989 | Crawford et al. | |
| 4,894,880 A | 1/1990 | Aznavoorian | |
| 5,046,213 A | 9/1991 | Curtis et al. | |
| D330,286 S | 10/1992 | Curtis et al. | |
| 5,226,206 A | 7/1993 | Davidovitz et al. | |
| 5,335,389 A | 8/1994 | Curtis et al. | |
| 5,359,747 A | 11/1994 | Amakasu | |
| 5,383,242 A | 1/1995 | Bigler et al. | |
| 5,392,483 A | 2/1995 | Heinzelman et al. | |
| 5,404,608 A | 4/1995 | Hommann | |
| 5,446,940 A | 9/1995 | Curtis et al. | |
| 5,465,444 A | 11/1995 | Bigler et al. | |
| 5,504,959 A | 4/1996 | Yukawa et al. | |
| 5,524,312 A | 6/1996 | Tan et al. | |
| 5,617,601 A | 4/1997 | McDougall | |
| 5,732,432 A | 3/1998 | Hui | |
| 5,836,030 A | 11/1998 | Hazeu et al. | |
| 5,987,681 A * | 11/1999 | Hahn et al. | 15/22.1 |
| 6,006,394 A | 12/1999 | Bredall et al. | |
| D434,563 S | 12/2000 | Lim et al. | |
| 6,178,579 B1 | 1/2001 | Blaustein et al. | |
| 6,189,693 B1 | 2/2001 | Blaustein et al. | |
| 6,360,395 B2 | 3/2002 | Blaustein et al. | |
| 6,371,294 B1 | 4/2002 | Blaustein et al. | |
| 6,381,795 B1 | 5/2002 | Hoffman et al. | |
| 6,836,917 B2 | 1/2005 | Blaustein et al. | |
| 2003/0226223 A1 | 12/2003 | Chan | |

FOREIGN PATENT DOCUMENTS

WO    WO 99/23910 A1    5/1999

* cited by examiner

Primary Examiner—Shay L Karls
(74) Attorney, Agent, or Firm—K. Bradford Adolphson

(57) ABSTRACT

An electric toothbrush is disclosed comprising a body, a head, and a neck extending therebetween. A motor, drive train, and one or more batteries impart motion to the collection of movable bristles. A spring component is provided in the drive train that is configured to absorb excessive loads that would otherwise be transmitted to the motor. Reducing or eliminating application of such excessive loads on the motor extends battery life.

12 Claims, 7 Drawing Sheets

ELECTRIC TOOTHBRUSH HAVING A FLEXIBLE DRIVE SHAFT

CROSS REFERENCE TO RELATED APPLICATION

This application claims the benefit of U.S. Provisional Application No. 60/545,325, filed Feb. 17, 2004.

FIELD OF THE INVENTION

The present invention relates to the field of toothbrushes, and more particularly, the invention relates to the field of electrically powered toothbrushes.

BACKGROUND OF THE INVENTION

Toothbrushes have traditionally utilized one or more groups of bristles that are fixed or otherwise attached to the head or end of the toothbrush. Toothbrushes are also known that utilize movable bristle sets or holders that are mechanically or electrically powered. Typically, an electric motor and a drive mechanism are retained within the body of the toothbrush and are coupled to the movable bristle sets or holders. Upon actuation of the motor and drive mechanism, the bristle holders may undergo a variety of different types of motion. Typically, one or more batteries are also provided within the body of the toothbrush to power the drive mechanism and impart motion to the movable bristle holders.

During operation of an electric toothbrush, power consumption of the electric motor is generally a function of the rate of rotation and load placed upon the motor by the drive mechanism. These parameters are dependent upon the load placed upon the brushing elements, e.g. the moving bristle holders, disposed on the brush head. It is also known that power consumption of the electric motor is also dependent upon the mechanical strain placed upon the motor, and typically, upon the output shaft of the motor.

A significant disadvantage in using an electric toothbrush is that after some time period of repeated use, the batteries are exhausted and must be replaced. In addition to the increasingly high cost of batteries, battery replacement is often regarded by consumers as burdensome or annoying. In addition, in certain low cost disposable electric toothbrushes, the batteries may be sealed within the body of the toothbrush and not be suitable for replacement. Accordingly, a need exists for extending battery life and the time period between battery replacement in an electric toothbrush.

Additionally, a need remains for an improved technique and assembly for increasing battery life in an electric toothbrush, particularly for instances besides those involving excessive strain or bending of a brush head or neck.

SUMMARY OF THE INVENTION

In a first aspect, the present invention provides an electric toothbrush comprising a handle having a hollow interior region with a motor disposed therein. The electric toothbrush also comprises a head comprising a movable bristle holder, wherein the movable holder has bristles disposed thereon. The toothbrush additionally comprises a neck extending between the handle and the head. And, the toothbrush comprises a drive shaft defining a longitudinal axis. The drive shaft extends through the neck and operatively connects the motor to the bristle holder. The drive shaft comprises a spring element.

In another aspect, the present invention provides an electric toothbrush comprising a handle defining a hollow interior region with a motor disposed therein. The electric toothbrush also comprises a head including a movable portion, wherein the movable portion comprises bristles. The toothbrush also comprises a neck extending between the handle and the head. And, the electric toothbrush further comprises a drive shaft comprising a spring element and defining a longitudinal axis. The drive shaft extends through the neck and operatively connects the motor to the movable portion of the head. Upon activation of the motor, the drive shaft undergoes reciprocating motion.

In yet another aspect, the present invention provides an electric toothbrush comprising a handle having a hollow interior region with a motor disposed therein. The toothbrush further comprises a head having a movable bristle holder, wherein the movable bristle holder has bristles disposed thereon. The toothbrush also comprises a neck extending between the handle and the head. And, the toothbrush comprises a drive shaft defining a longitudinal axis. The drive shaft extends through the neck and operatively connects the motor to the movable bristle holder. The drive shaft comprises a spring element that is substantially rigid and unchanged in shape when the motor is not excessively loaded and relatively flexible upon application of an excessive load to the motor.

In still a further aspect, the present invention provides an electric toothbrush comprising a handle defining a hollow interior with a motor disposed therein. The toothbrush also comprises a head including a movable bristle holder which has bristles disposed thereon. The toothbrush also comprises a neck extending between the handle and the head. And, the toothbrush comprises a drive shaft extending through the neck and operatively connecting the motor to the bristle holder. The drive shaft comprises a spring element. Upon operation of the toothbrush and application of an excessive load to the bristle holder, the motor continues to operate and causes the spring element to undergo repeated displacements.

BRIEF DESCRIPTION OF THE DRAWINGS

The present invention may take form in various components and arrangements of components, and in various techniques, methods, or procedures and arrangements of steps. The referenced drawings are only for purposes of illustrating embodiments of the toothbrush according to the present invention, they are not necessarily to scale, and are not to be construed as limiting the present invention.

It is believed that the present invention will be better understood from the following description taken in conjunction with the accompanying drawings in which.

DETAILED DESCRIPTION OF THE INVENTION

Figure 1:
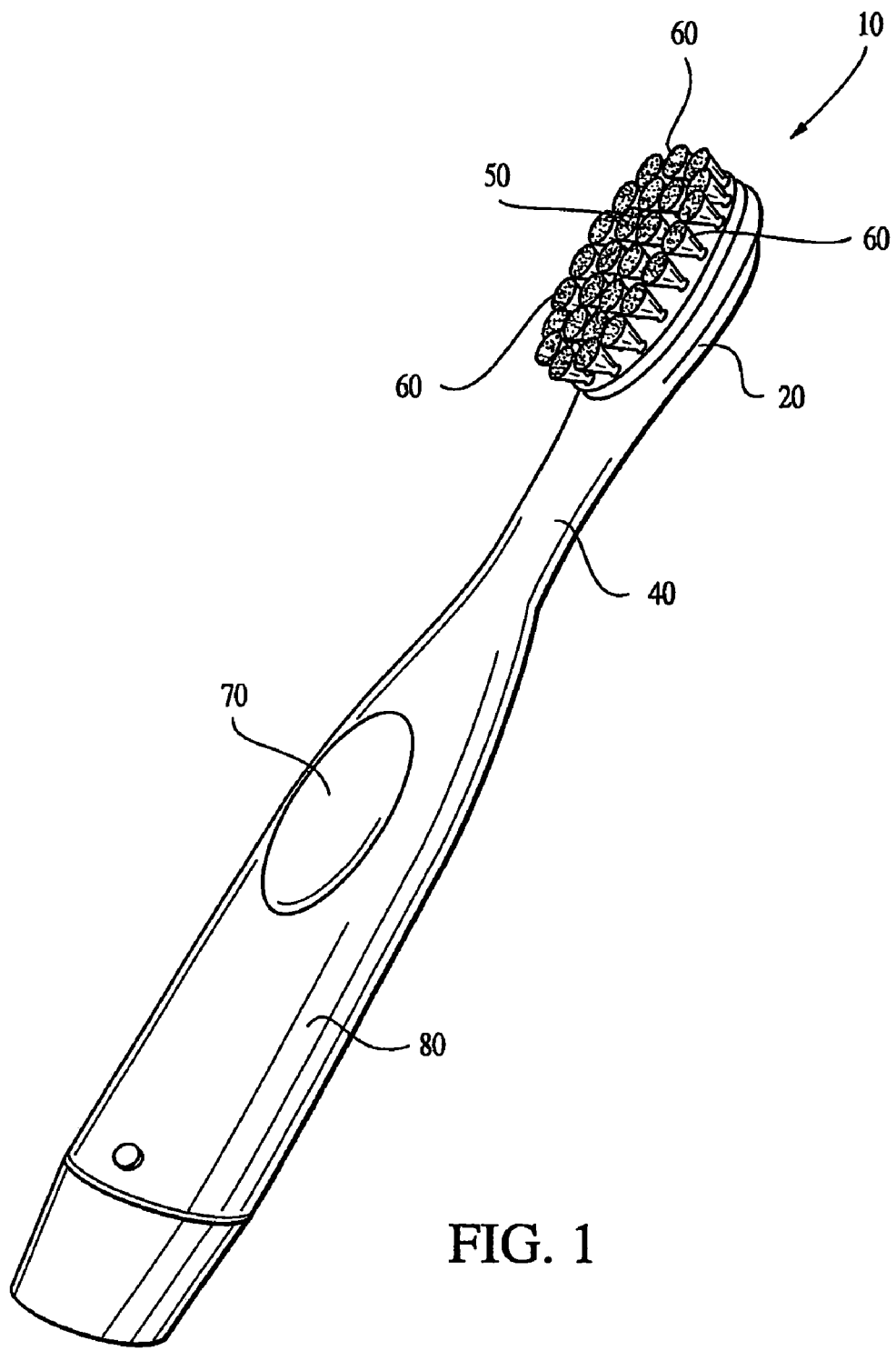
FIG. 1 is a perspective view of a toothbrush in accordance with the present invention.

In accordance with the present invention, it has been discovered that battery life in an electric toothbrush can be significantly extended if the load placed upon an electric motor in the toothbrush is regulated. For example, application of an excessive load that stalls or substantially stalls the motor, may consume excessive power. The present invention provides a drive mechanism component, or components, that can limit the load that is applied to the electric motor and prevents stalling by absorbing this excess load, and thereby extends battery life. In the embodiments described herein, these components are springs or spring elements that are provided along a portion of a drive shaft in the drive mechanism. When choosing a spring element the spring constant can be considered. Choosing a spring constant that results in a toothbrush drive shaft that is too flexible can result in insufficient cleaning force applied to the teeth. However, choosing a spring constant that results in a drive shaft that is too rigid, can result in the spring element not absorbing the excessive load, thereby transmitting this load to the motor and failing to prevent the motor from stalling.

As noted, application of an excessive load to the brush head can consume inordinate or excessive amounts of power from one or more batteries used to power the toothbrush. Generally, an "excessive load," as that term is used herein, is one that when applied to the drive shaft of the toothbrush, results in substantial stalling of the motor. This stalling of the motor results in a reduction in the rate of movement of the movable bristle holder by about 50% to less than about 100%, and typically by about 75% to about 95% and can result in shortened battery life. For example, in one embodiment a toothbrush exhibits a brushing rate, without application of any load to the brush head, of about 250 to about 5000 stroke cycles per minute, in another embodiment the toothbrush exhibits a brushing rate of from about 750 to about 2000 strokes per minute, and in yet another embodiment the toothbrush exhibits a brushing rate of about 1250 strokes per minute. A "stroke" as used herein, is one complete cycle of movement. For a reciprocating drive shaft, a stroke includes travel in a first direction and then travel in a second, opposite direction. Upon brushing or application of a normal or typical brushing load to the bristle holders, the brushing rate can decrease to about 625 strokes per minute for a toothbrush exhibiting a brushing rate of about 1250 strokes per minute. However, upon application of greater brushing loads, the brushing rate further decreases. In the present example, the brushing load would be deemed as "excessive" when the rate slowed to about 315 strokes per minute (corresponding to a 75% reduction in brushing rate).

The spring portion is formed or otherwise provided along a portion of the length of the drive shaft such that during operation of the toothbrush and upon application of an excessive load to the brushing end of the drive shaft, the spring is displaced thereby absorbing a portion of the load. This in turn reduces the expression or transmission of the otherwise excessive load at the other end of the drive shaft, i.e. the motor end of the drive shaft. The term "brushing end" of the drive shaft refers to the end of the drive shaft that is proximate the movable bristle holder driven by the drive shaft and is operatively connected to the holder. And, the term "motor end" of the drive shaft refers to the end of the drive shaft that is proximate the electric motor that ultimately drives the drive shaft. As previously described, it is the application of an excessive load upon the motor that results in excessive power consumption. And so, by reducing or avoiding the application of excessive loads upon the motor, i.e. by provision of the spring portion, excessive power consumption is avoided.

The spring portion is formed or otherwise provided along a portion of the drive shaft such that during normal use of the toothbrush, and without an excessive load being placed thereon, the spring is not displaced, nor displaced to any significant extent. This characteristic of the spring, during normal operation of the toothbrush, is also described as the spring remaining essentially rigid and unchanged in shape.

FIG. 1 is a perspective view of an embodiment of the toothbrush 10 in accordance with the present invention. The toothbrush 10 comprises a body 80, a head 20, and a neck 40 extending between the handle or body 80 and the head 20. An actuator 70 or switch is provided along the body 80. Disposed on the head 20 are a plurality of fixed bristles 60 and a collection of movable bristles 50, both of which are described and illustrated in detail by the various patents incorporated herein by reference.

Figure 2:
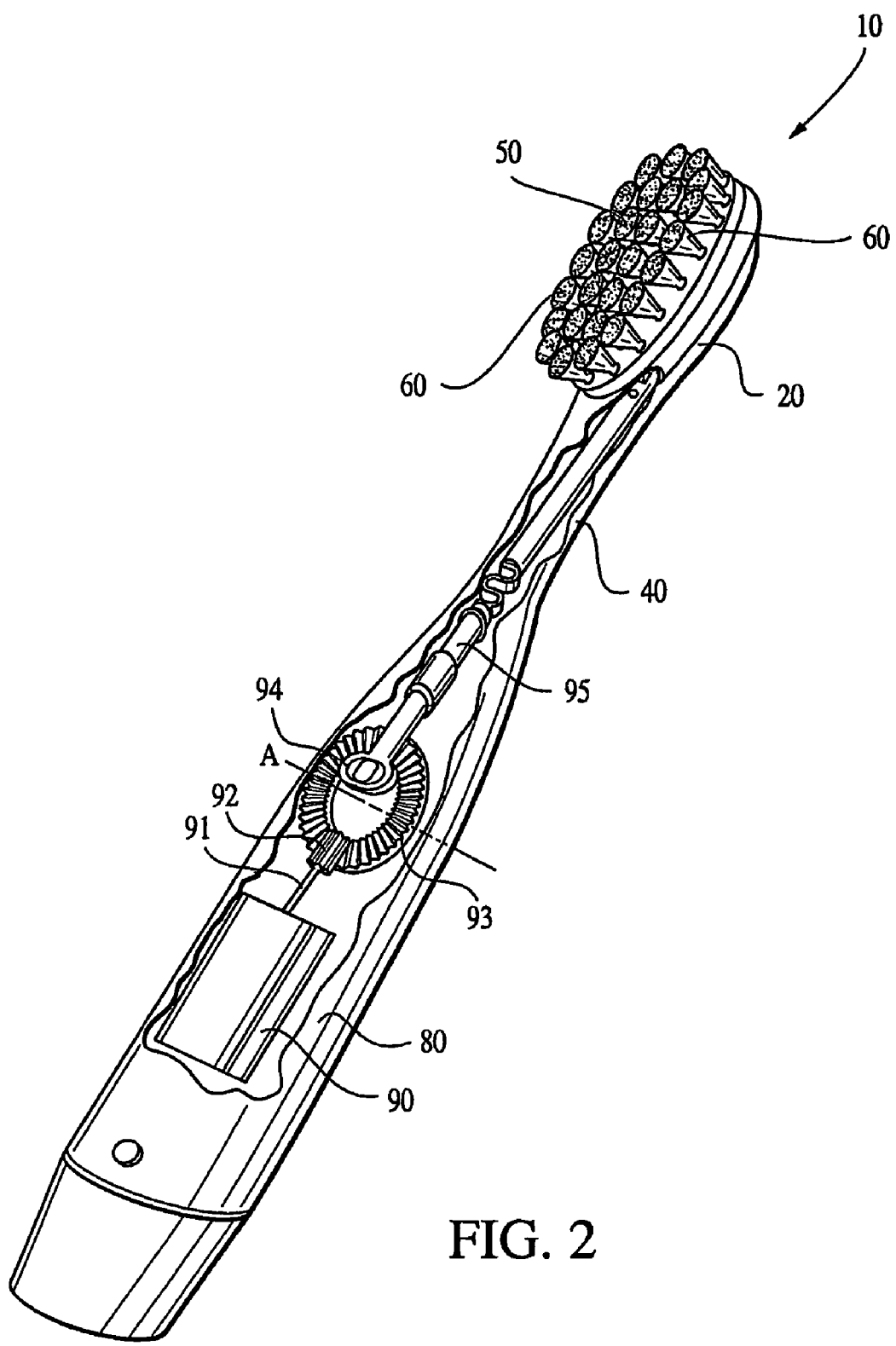
FIG. 2 is a partial fragmentary perspective view of the toothbrush, illustrated in FIG. 1.

FIG. 2 is a partial fragmentary view of an embodiment of the toothbrush 10 shown in FIG. 1. FIG. 2 illustrates a motor 90 and a drive train or mechanism retained within the body 80 that are used to move the collection of movable bristles 50 disposed on the brush head 20. The movable bristles are attached to and supported by a movable bristle holder (not shown in FIG. 2). Upon activation of actuator 70 (shown in FIG. 1) disposed along the body 80 of the toothbrush 10, electrical energy such as from one or more batteries (not shown) in the housing 80, is directed to a motor 90. The motor 90 includes an output shaft 91 to which is affixed a drive gear 92. The drive gear 92 is engaged with a rotatable drive gear 93. The drive gear 93 is mounted such that it rotates about an axis A extending in a direction perpendicular to the output shaft 91 of the motor. The drive gear 93 includes a drive member 94 which is disposed on the drive gear 93 radially outward from the center of rotation, or axis A, of the drive gear 93. Attached to the drive member 94 is a drive shaft 95. This arrangement of drive components imparts reciprocating motion to the drive shaft 95 from a powered rotary output shaft 91.

A wide array of drive motor and gearing configurations may be utilized in the toothbrushes described herein. For example, various drive mechanisms described in U.S. Pat. Nos. 6,178,579; 6,189,693; 6,360,395; and 6,371,294, all of which are hereby incorporated by reference, may be utilized.

As will be appreciated, the movable bristles are disposed and generally supported on one or more movable bristle holders. The movable bristle holder may undergo a wide variety of motions. The movable bristle holder may undergo angular motion, linear motion, or curvilinear motion. The movement of the bristle holder may be constant or periodic. In one embodiment, the motion of the movable bristle holder is periodic linear motion or reciprocation.

Figure 3:
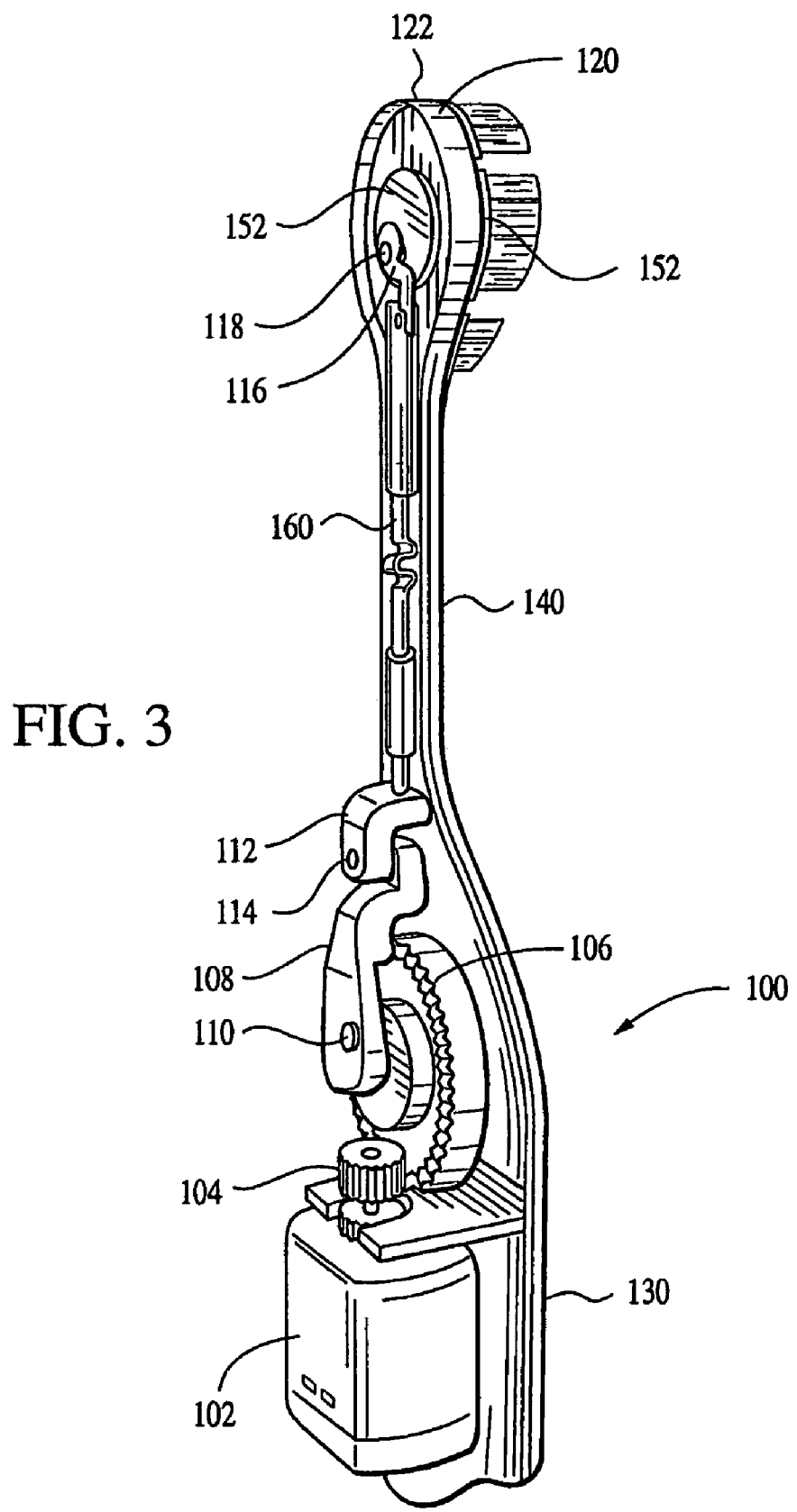
FIG. 3 is a perspective view showing a partial assembly of another toothbrush in accordance with the present invention.

Another embodiment of the toothbrush using a reciprocating drive shaft is illustrated in FIG. 3. FIG. 3 illustrates an electric toothbrush 100 comprising a toothbrush head 120, a body or handle 130, and an elongated neck 140 extending therebetween. The drive train, which includes various shafts and gears that transmit motion from a motor to an inner movable bristle holder 152, is similar to that described in U.S. Pat. No. 6,178,579. The handle 130 is hollow and includes a motor 102 and batteries (not shown) for powering the motor. A rechargeable power source can be substituted for the batteries. The head 120 has a longitudinal axis extending therethrough. The longitudinal axis extends in the same general longitudinal direction as a longitudinal axis of the shaft 160. The inner movable bristle holder 152 is disposed along the head 120, wherein the end 122 is at the distal most point of the head 120. Although in one embodiment the inner movable bristle holder 152 is oval in shape, other shapes can be utilized. Further, while the inner movable bristle holder 152 is disposed proximate the end 122 of the head 120, it will be appreciated that the movable bristle holder 152 can be disposed away from the end 122 and other features, such as stationary bristles, can be disposed around at least a portion of the perimeter of the inner movable bristle holder 152. In this embodiment, the inner movable bristle holder 152 reciprocates.

A first gear 104 is operatively connected to and powered by the motor 102. A second gear 106 is operatively connected to the first gear 104. The rotational axis of the second gear 106 is approximately normal to the rotational axis of the first gear 104 such that the teeth of the first gear 104 mesh with teeth of the second gear 106, thus causing second gear 106 to rotate as the first gear 104 rotates.

A first arm 108 is eccentrically and pivotably connected to the second gear 106 via a pin 110 or other fastening device. Due to the eccentric connection, the rotational motion of the second gear 106 is converted into a reciprocating motion of the first arm 108. A second arm 112 is pivotably connected to the first arm 108 via a pin 114 or other fastening device. The shaft 160 is fixedly secured, such as by a press fit, to the second arm 112. The shaft 160 is housed at least partially within the neck 140. The shaft 160 is also engaged with a third arm 116. The third arm 116 is connected at its terminal end to the inner bristle holder 152 via a pin 118 or other fastening device. The terminal end of the third arm 116 is offset from the longitudinal axis of the shaft 160 so that it is pinned adjacent the outer periphery of the inner bristle holder 152. This offset arrangement converts the reciprocating motion of the third arm 116 into a reciprocating motion of the inner bristle holder 152, wherein the inner bristle holder 152 reciprocates about an axis approximately parallel to the longitudinal axis of the shaft 160.

Figure 4:
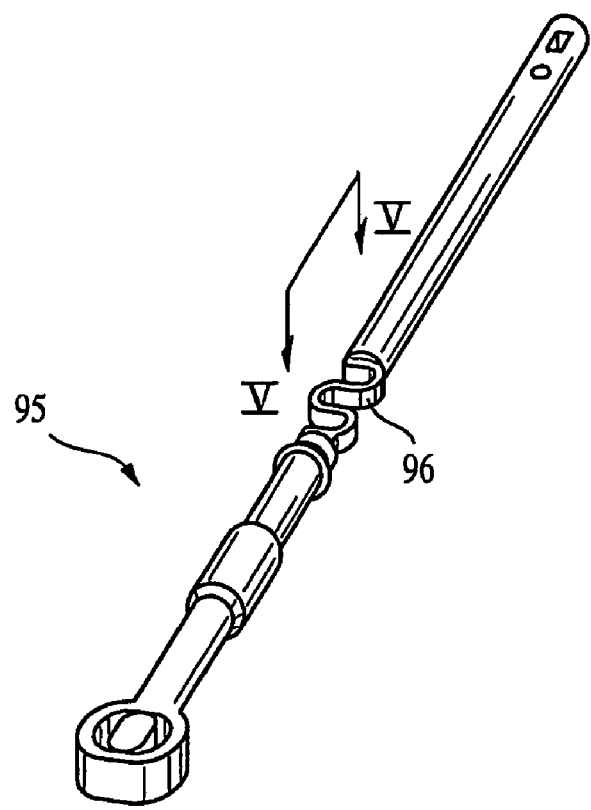
FIG. 4 is a perspective view of a drive shaft in accordance with the present invention.
Figure 5:
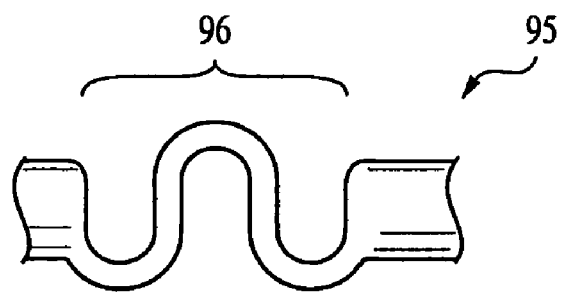
FIG. 5 is a detailed, partial side view of a spring portion of the drive shaft shown in FIG. 4.

Both embodiments of the drive mechanisms illustrated in FIGS. 2 and 3 utilize a drive shaft having a spring component or spring element provided along at least a portion of the drive shaft. More specifically, FIGS. 4 and 5 illustrate an embodiment of the drive shaft 95 in accordance with the present invention. The drive shaft 95 is utilized in the embodiment of the toothbrush depicted in FIGS. 1 and 2. The drive shaft 95 includes a spring portion, element, or component 96 along at least a portion of its length. In one embodiment the spring portion 96 is integrally formed as part of the drive shaft. In another embodiment the drive shaft 95 including the spring portion 96 is a one piece unit. The drive shaft 160 illustrated in FIG. 3 also features a spring portion, element, or component along at least a portion of its length. The description of this spring component is the same as the following description for spring 96 provided with drive shaft 95.

The specific type of load applied to the spring element during use of the toothbrush may be either compressive or tensile. That is, during normal use of the brush, either a compressive load or a tensile load may be placed upon the spring. Typically, the application of these loads will alternate as the drive shaft reciprocates. For example, after the application of a tensile load, a compressive load is then applied; afterwhich a tensile load is then applied etc. As previously explained, if an excessive load is placed upon the spring, the spring may be either compressed or extended depending upon whether the load is compressive or tensile.

The degree to which the spring is compressed or extended, depends upon the magnitude of the excessive load, the stroke length and the characteristics of the spring. Before describing these aspects in greater detail, it is instructive to consider springs, their characteristics, and behavior.

Springs are fundamental mechanical components which form the basis of many mechanical systems. A spring can be defined to be an elastic member which exerts a resisting force when its shape is changed. Most springs are assumed linear and obey Hooke's Law:

$$F = k\Delta$$

In this equation, F is the resisting force, $\Delta$ is the displacement of the spring, and the k is the spring constant.

For a non-linear spring, the resisting force is not linearly proportional to its displacement. The embodiments described herein utilize linear springs. However, the present invention includes the use of non-linear springs.

To choose a spring constant the motor and the structural arrangement of the motor and drive shaft can be considered. Although, other forces can be considered depending on the characteristics of the motor, generally a force of between about 1 to about 15 Newtons is an excessive force, and therefore can stall the motor. A load of about 1 to about 15 Newtons applied to the head of the toothbrush may translate to a load of about 1 to about 15 Newtons on the drive shaft of the toothbrush depending on the type and manner of connection between the drive shaft and the movable bristle holder. On account of the variety of motors available, one method of choosing a spring constant which can absorb the excess load of a particular motor involves first determining what load will stall the motor. To determine this load in a toothbrush having a reciprocating shaft, one can attach a drive shaft to the motor and apply load to the drive shaft until the motor stalls. This is the maximum load required to stall the motor. This load in combination with the stroke length can then be used to calculate the maximum desired spring constant. The maximum desired spring constant will only flex to absorb the stroke length of the movable bristle holder when the load has reached the level required to stall the motor. The minimum desired spring constant is based upon the load necessary to get desired mouth feel and cleaning capabilities. The closer the spring constant is to the minimum desired spring constant the less of a load is required to result in flexing of the spring element of the drive shaft. However, this likely results in minimized cleaning capabilities, as the spring absorbs all load originating from the motor, and no movement of the drive shaft is translated to the movable bristle holder on the head of the toothbrush. Additionally, the extension of battery life is diminished the closer the spring constant is to the maximum desired spring constant as the spring element will not absorb any excess load until the maximum load to stall the motor is reached. In one embodiment the spring constant may be less than about 100%, 90%, 80%, 75%, 65%, and 50% of the maximum spring constant and/or greater than about 25%, 35% 45% and 55% of the minimum spring constant.

Another embodiment of the present invention utilizes a spring or spring element in a drive shaft, in which the spring exhibits a spring constant of from about 4 to about 8 N/mm, in another embodiment the spring or spring element exhibits a spring constant of from about 5 to about 7 N/mm, and in yet another embodiment the spring constant is about 6 N/mm. It will be understood however that the present invention includes the use of springs having spring constants greater than, or lesser than these representative values. For example, it is contemplated that springs having a spring constant of greater than about 0.1, 0.5, 1.0, 1.5, 2.0, 2.5, 3.0, 3.5, and 8.5, 9.0, 9.5, 10 N/mm and higher could be utilized in a drive mechanism.

Utilizing a spring constant of 4 N/mm will result in the following approximate relationships set forth in Table 1 between force applied at the brushing end of the drive shaft and the displacement of the spring.

TABLE 1

Relationship Between Applied Force and Spring Displacement for k = 4 N/mm

| Force (F) | Displacement (Δ) |
|---|---|
| 1 N | 0.25 mm |
| 2 | 0.50 |
| 3 | 0.75 |
| 4 | 1.00 |
| 5 | 1.25 |
| 6 | 1.50 |
| 7 | 1.75 |
| 8 | 2.00 |
| 9 | 2.20 |
| 10 | 2.50 |

Utilizing a spring having a spring constant of 5 N/mm will result in the following approximate relationships set forth in Table 2 between force applied at the brushing end of the drive shaft and the displacement of the spring.

TABLE 2

Relationship Between Applied Force and Spring Displacement for k = 5 N/mm

| Force (F) | Displacement (Δ) |
|---|---|
| 1 N | 0.20 mm |
| 2 | 0.40 |
| 3 | 0.60 |
| 4 | 0.80 |
| 5 | 1.00 |
| 6 | 1.20 |
| 7 | 1.40 |
| 8 | 1.60 |
| 9 | 1.80 |
| 10 | 2.00 |

And, utilizing a spring having a spring constant of 6 N/mm, leads to the following relationship between force and spring displacement, as shown in Table 3.

TABLE 3

Relationship Between Applied Force and Spring Displacement for k = 6 N/mm

| Force (F) | Displacement (Δ) |
|---|---|
| 1 N | 0.17 mm |
| 2 | 0.33 |
| 3 | 0.50 |
| 4 | 0.67 |
| 5 | 0.80 |
| 6 | 1.00 |
| 7 | 1.17 |
| 8 | 1.33 |
| 9 | 1.50 |
| 10 | 1.67 |

Utilizing a spring having a spring constant of 7 N/mm will result in the following approximate relationships set forth in Table 4 between force applied at the brushing end of the drive shaft and the displacement of the spring.

TABLE 4

Relationship Between Applied Force and Spring Displacement for k = 7 N/mm

| Force (F) | Displacement (Δ) |
|---|---|
| 1 N | 0.14 mm |
| 2 | 0.29 |
| 3 | 0.43 |
| 4 | 0.57 |
| 5 | 0.72 |
| 6 | 0.86 |
| 7 | 1.00 |
| 8 | 1.14 |
| 9 | 1.29 |
| 10 | 1.43 |

Utilizing a spring having a spring constant of 8 N/mm will result in the following approximate relationship set forth in Table 5 between force applied at the brushing end of the drive shaft and displacement of the spring.

TABLE 5

Relationship Between Applied Force and Spring Displacement for k = 8 N/mm

| Force (F) | Displacement (Δ) |
|---|---|
| 1 N | 0.13 mm |
| 2 | 0.25 |
| 3 | 0.38 |
| 4 | 0.50 |
| 5 | 0.63 |
| 6 | 0.75 |
| 7 | 0.88 |
| 8 | 1.00 |
| 9 | 1.13 |
| 10 | 1.25 |

In accordance with the present invention, various approaches are provided for designing a spring element for a reciprocating drive shaft. That is, by selection of a suitable material for the spring and appropriate design of the shape or configuration of the spring, a proper spring constant can be achieved. A proper spring constant is one that corresponds to the spring being displaced at least a portion of the "stroke length" of the drive shaft upon application of an excessive load. The term "stroke length" as used herein refers to the maximum linear distance that the drive shaft travels in one direction during a reciprocation cycle. In one embodiment of the toothbrush the stroke length of the bristle holder can be from about 0.5 mm to about 3 mm, in another embodiment the stroke length of the bristle holder can be from about 0.75 mm to about 2.0 mm, in another embodiment the stroke length of the bristle holder can be from about 0.75 mm to about 1.0 mm, and in yet another embodiment the stroke length of the bristle holder can be about 0.85 mm.

Although many springs exhibit a spring constant that is the same or substantially the same regardless of whether the applied load is tensile or compressive, one type of spring in accordance with the present invention exhibits different spring constants for tensile loads and compressive loads. In one embodiment the spring can absorb at least the stroke length of the drive shaft.

Testing was performed in which the resulting spring displacement from application of an excessive load to a spring element according to the present invention was investigated. In that testing, one end of the spring was fixed, and the other opposite end received a particular force. For a maximum excessive tensile force of about −1.4 pounds (−6.23 N), the spring was extended by about 0.85 mm. And, for a maximum excessive compressive force of about 0.95 pounds (4.23 N), the spring was compressed by about 0.80 mm. The amount of force as measured at the drive shaft corresponding to these excessive loads is about 1.2±0.30 pounds (5.34±1.33 Newtons) of force. Calculating a spring constant k from these values of displacement and force, results in k=6.28±1.56 N/mm.

In one exemplary embodiment according to the present invention, a spring element is incorporated into a drive shaft of a reciprocating drive mechanism. The drive shaft, during operation of the toothbrush, exhibits a stroke length of about 0.85 mm. The material(s) and geometry of the spring are selected such that upon application of an excessive load to the brush head while brushing, the spring is compressed and extended, in each direction by the stroke length. This enables the motor to continue to operate while consuming ordinary levels of power from the battery. And, furthermore, the material(s) and geometry of the spring are selected such that upon application of loads to the brush head less than those deemed excessive; the spring is not displaced to any appreciable extent. This enables the drive shaft to reciprocate and transfer power without any significant loss in efficiency from its motor end, through and across the spring, to the brushing end of the drive shaft.

Although not wishing to be limited to any particular theory or design approach, an approximate relationship has been identified between excessive brushing loads as measured on a bristle holder in one embodiment of a brush head, and that load as expressed at the brushing end of the drive shaft. Generally, in that particular electric toothbrush embodiment utilizing a reciprocating drive mechanism that powers a movable bristle holder, application of a brushing load of about 3 pounds on the bristle holder corresponds to a load of about 1 pound as measured at the brushing end of a drive shaft. The 3 pound load is applied to the bristle holder as a compressive force on the bristles and thus in turn, on the bristle holder, generally in a direction that is perpendicular to the longitudinal axis of the toothbrush. Application of this load increases friction between the reciprocating bristle holder and the surfaces that it contacts. The resulting load exhibited at the brushing end of the drive shaft, upon application of the about 3 pound brushing load to the bristle holder, is about 1 pound. This about 1 pound of force may be considered as the amount of force necessary to overcome the increased friction of the bristle holder resulting from the about 3 pound load placed thereon. The about 1 pound of force is generally directed along the longitudinal axis of the reciprocating drive shaft.

The characteristics and behavior of springs are generally dependent upon the material from which the spring is formed, and the geometry, e.g. shape or configuration, of the spring. In order to provide a suitable spring portion in a drive shaft according to the present invention, a spring may be formed into a relatively flexible shape using a relatively non-flexible or stiff material. Alternatively, the spring may be formed into a relatively non-flexible shape using a relatively flexible material. And, the spring may be formed into a relatively flexible shape using a relatively flexible material. Moreover, the spring may be formed into a relatively non-flexible shape and formed from a relatively non-flexible material. This latter set of characteristics would likely not be preferred due to the very large spring constants resulting therefrom.

Specifically, the drive shaft and spring may be formed from a variety of materials. In one embodiment, the drive shaft and spring are formed from the same material. The drive shaft and spring can be formed from a polymeric material that exhibits sufficient strength and rigidity to transfer power from the motor to one or more movable bristle holders disposed on the head of the toothbrush without undergoing significant deformation during normal operations of the toothbrush. Examples of suitable polymeric materials include, but are not limited to, self-lubricating materials; polymeric materials such as ABS, nylon, PPE, POM (a polyoxymethylene copolymer), and Delrin® acetal resins available from DuPont®; and metals such as steel and aluminum. An example of a commercially available nylon is PA6 nylon, available from DuPont. It is also contemplated to utilize other materials for forming the drive shaft and spring. Examples of materials that can be utilized in the inventive toothbrush include, but are not limited to, those discussed in U.S. application Ser. No. 10/659,489 the substance of which is incorporated by reference herein. Furthermore, it may be desirable to provide a low friction coating on the exterior surface of the drive shaft and/or the spring to minimize friction between that component and the interior walls of the cavity defined within the neck.

Figure 6:
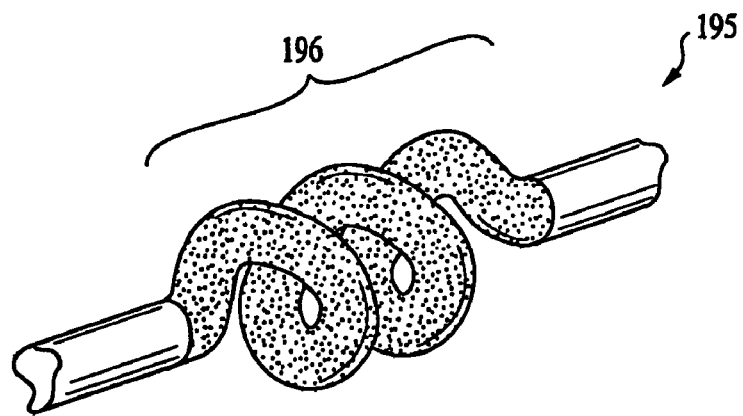
FIG. 6 is a detailed partial perspective view of an alternate drive shaft and spring portion in accordance with the present invention.
Figure 7:
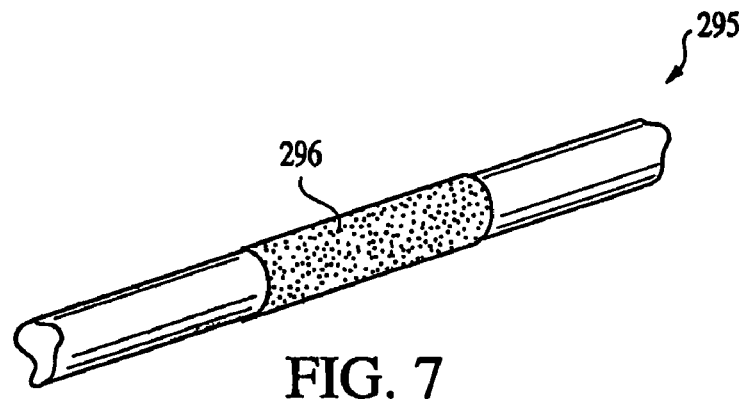
FIG. 7 is a detailed partial perspective view of an alternate drive shaft and spring portion in accordance with the present invention.
Figure 8:
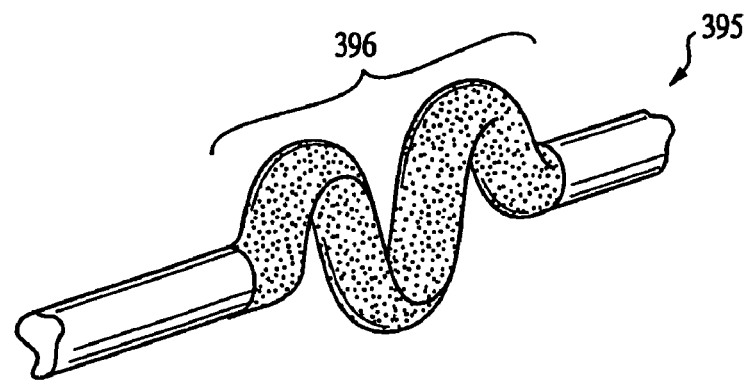
FIG. 8 is a detailed partial perspective view of an alternate embodiment drive shaft and spring portion in accordance with the present invention.

The present invention also encompasses embodiments in which the drive shaft and spring portion are formed from different materials, materials differing in their flexibility, rigidity, or other physical properties. FIG. 6 illustrates a spring portion 196 formed from a material different than the material forming a drive shaft 195. FIG. 7 illustrates an alternate embodiment drive shaft 295 having a spring portion 296 formed from a material different than the material constituting the drive shaft 295. In this embodiment, it will be appreciated that the spring function is provided by appropriate selection of the material forming the spring portion 296 as opposed to that function resulting from the configuration or shape of the portion 296. FIG. 8 illustrates yet another alternate embodiment of a drive shaft 395 having a spring portion 396 formed from a different material. Viewing FIGS. 7 and 8 collectively, it will be appreciated for example, that in the event that the materials forming springs are the same, the spring characteristics may be varied by appropriate choice of the shape or configuration of the spring. Furthermore, in the event that the shape or configuration of the springs is the same, the spring characteristics may be varied by appropriate choice of materials that form the springs.

Figure 9:
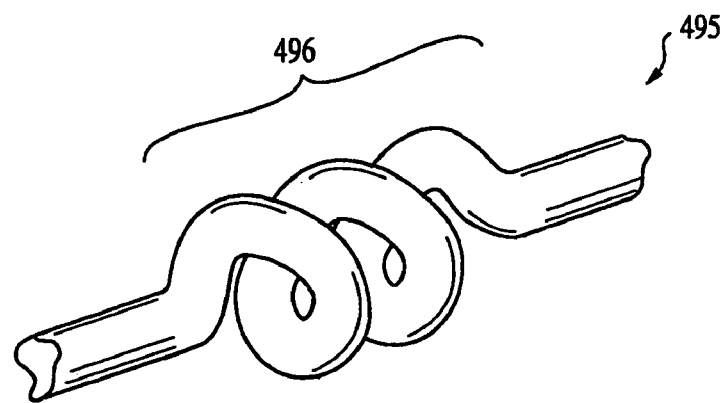
FIG. 9 is a detailed partial perspective view of an alternate drive shaft and spring portion in accordance with the present invention.

The present invention also encompasses spring elements utilized in conjunction with drive mechanisms utilizing a rotary drive shaft. For example, a torsional or coil spring could be incorporated along a portion of a rotary drive shaft as previously shown in FIG. 6. FIG. 9 illustrates an alternate embodiment drive shaft 495 having a coil spring 496 in which both the coil spring and the drive shaft are formed from the same material. During normal operation of the toothbrush, the spring 496 would not undergo any significant rotational deformation and so, efficiently transfer rotary power from one end of the drive shaft to the other. However, upon application of an excessive load, the spring would deform, i.e. undergo torsional deformations, to thereby limit or otherwise reduce the load placed upon the motor. This, as described herein, reduces power consumption from the battery.

Figure 10:
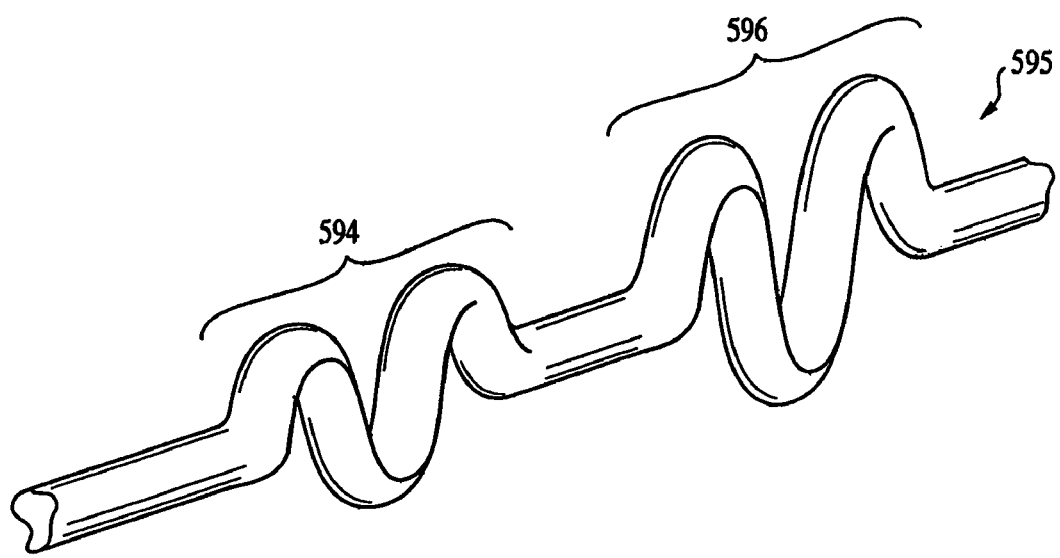
FIG. 10 is a detailed partial perspective view of an alternate drive shaft and spring portions in accordance with the present invention.

The present invention also encompasses the use of two or more springs or spring elements in a drive mechanism of an electric toothbrush. The provision of two or more springs enables the drivetrain to be particularly adapted to absorb excessive loads at certain operating conditions, or particular ranges or magnitudes of loads. Moreover, each of the springs may be of a different size, type or configuration; may exhibit a different spring constant; may be formed from different materials; or may be positioned at different locations along the drive mechanism or drive shaft. For example, FIG. 10 illustrates an embodiment of the drive shaft 595 comprising a first spring 594 and a second spring 596. The springs 594 and 596 exhibit different spring characteristics. In the embodiment depicted in FIG. 10, the drive shaft 595 and the springs 594 and 596 are all formed from the same material. However, due to the size and/or configurational differences between the springs 594 and 596, the two springs have different spring constants.

Figure 11:
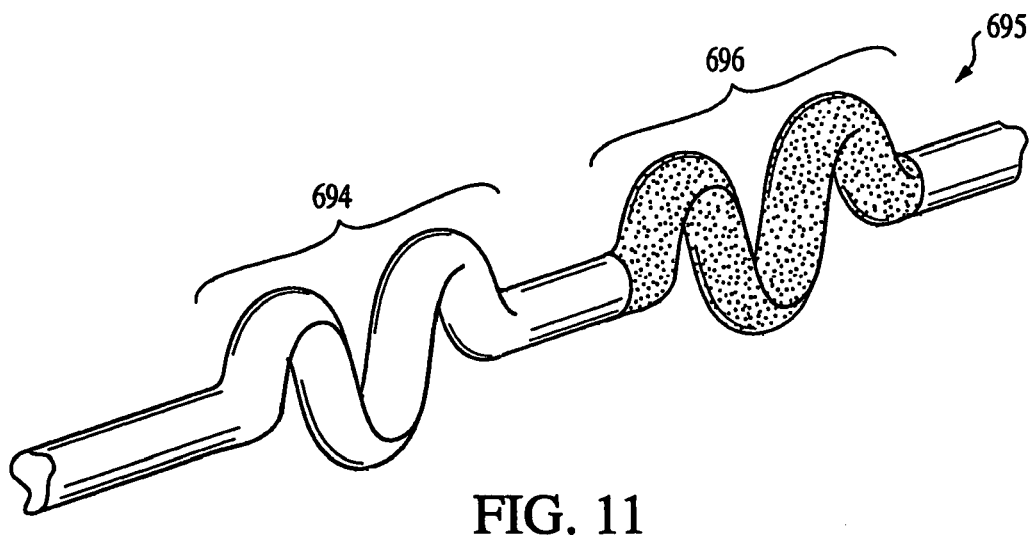
FIG. 11 is a detailed partial perspective view of an alternate drive shaft and spring portions in accordance with the present invention.
Figure 12:
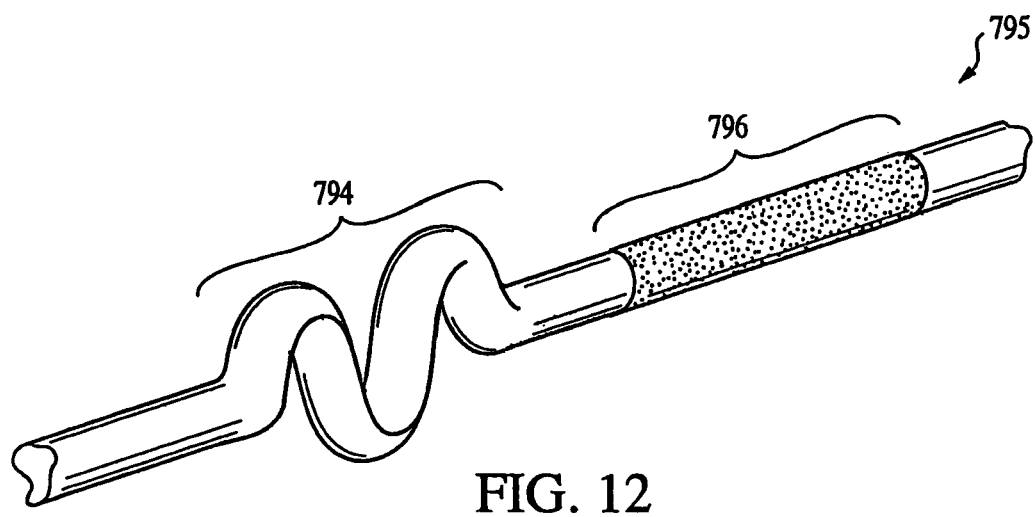
FIG. 12 is a detailed partial perspective view of an alternate drive shaft and spring portions in accordance with the present invention.
Figure 13:
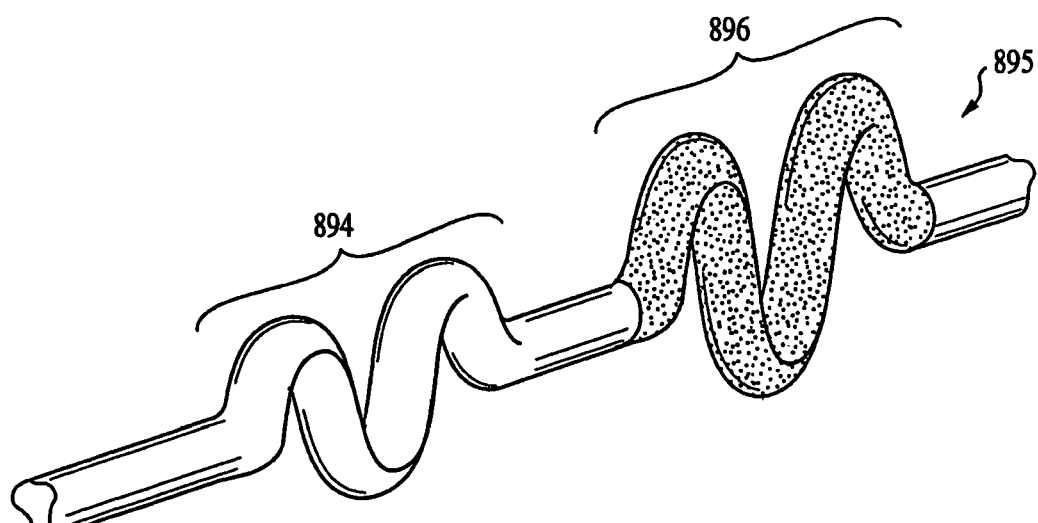
FIG. 13 is a detailed partial perspective view of an alternate drive shaft and spring portions in accordance with the present invention.

For a drive shaft comprising multiple springs or spring elements, the present invention also includes a strategy of forming one or more of the springs from a first material, and forming one or more of the other or remaining springs from a different material. Again, the materials selected for forming the springs may also be entirely different than the material constituting the drive shaft. FIG. 11 illustrates a drive shaft 695 comprising a first spring 694 and a second spring 696. The second spring 696 is formed from a different material than is used for the spring 694. As will be appreciated, generally, the materials selected for the springs 694 and 696 can be selected such that the springs exhibit different spring constants. It is also contemplated to provide a drive shaft with a spring element provided by a region of a different material. For instance, FIG. 12 illustrates a drive shaft 795 comprising a first spring 794 and a second spring 796. The material forming the second spring 796 is different than the material forming the spring 794 and the drive shaft 795. FIG. 13 illustrates a drive shaft 895 having multiple springs such as a first spring 894 and a second spring 896, each formed from a different material. It is also contemplated that the remaining portion of the drive shaft 895 is formed from another, different material. FIG. 13 also illustrates an aspect in which springs of a similar configuration, however of a different size, are provided on a drive shaft.

Another aspect included in the present invention is the selective orientation of a drive shaft having multiple springs or spring portions within a drive mechanism. Generally, depending upon the particular application, the drive shaft having multiple springs may be oriented within the drive train such that a particular spring is first exposed to loads applied to the brushing end of the drive shaft. Similarly, the various springs or spring elements may be disposed on the drive shaft in a particular sequence.

Although the embodiments described herein utilize spring portions or spring elements that are integrally provided as part of a drive shaft, the present invention includes embodiments in which a spring component is provided separate from the drive shaft. In such a configuration, a drive mechanism would utilize the spring component at a location between the motor output shaft and the one or more bristle holder(s) that are powered by the motor.

Moreover, although the embodiments of the toothbrushes described herein utilize a spring element disposed within the neck region of the toothbrush, the present invention includes embodiments in which the spring is disposed in other regions of the toothbrush. For example, the spring could be positioned or generally reside within the handle portion of the toothbrush. And, the spring could be provided in the head region of the toothbrush.

While brush heads of embodiments of the toothbrush have been illustrated for simplicity with tufts of bristles that extend in a direction substantially perpendicular to the longitudinal axis of the head from which they extend, it is contemplated that the bristles might be arranged differently to complement or further enhance the fixed bristles or the motion of the movable bristles. Some or all of the bristles might extend in a direction which forms an acute angle with a top surface of a bristle holder, and may extend in a forward or rearward direction. In another embodiment, some of the bristles might extend outwardly away from the head, in another direction, again forming an acute angle with respect to the top surface of the bristle holder. Massaging bristles or bristles of varying height might also be used, such as described in U.S. Pat. No. Des. 330,286, and Des. 434,563. Other bristle arrangements suitable for use include those arrangements described in whole or part in U.S. Pat. Nos. 6,006,394; 4,081,876; 5,046,213; 5,335,389; 5,392,483; 5,446,940; 4,894,880; and International Publication No. WO99/23910.

The inventive electric toothbrushes can be made with any combination of bristle or massaging tip types, dimensions, combinations, angles and arrangements. Tufts of bristles may alternate in height. In one embodiment there are a plurality of tall tufts and a plurality of shorter tufts. The difference in length between the tall tufts and the shorter tufts is between about 0.5 mm and about 2.5 mm in one embodiment and between about 1 mm and about 2 mm in other embodiments. The tall and short tufts of bristles can be provided with different characteristics. For example, the tall tufts of bristles may be relatively soft for gently cleaning and massaging gums of a user while shorter tufts of bristles may be somewhat firmer for interdental cleaning (or vice versa). This arrangement allows the longer (and typically softer) bristles to be pressed, bent and deflected against the gums of the user before the shorter (and typically firmer) bristles contact the teeth and gums of the user. Therefore, for example, soft bristles can be applied with more force while stiffer (and perhaps less comfortable) bristles are applied with less force.

In one embodiment, the present invention provides a bristle configuration in which the movable bristles, i.e. those supported by and secured to the movable bristle holder, have a total bristle length that is less than the length of the stationary bristles that at least partially encircle or extend alongside the movable bristle holder and bristles secured thereto. A further variation of this bristle configuration features a movable bristle holder that is slightly elevated above the outer surface of the head such that the distal tips of the movable bristles are approximately at the same height as the longer stationary bristles extending from the outer surface of the head. Generally, by utilizing movable bristles that have a relatively short length, the distance or stroke of the movable bristle holder (when undergoing a reciprocating motion) is less than if longer bristles were used. A shorter stroke generally leads to decreased power requirements. This is beneficial since battery demands are then reduced, which may further promote manufacturability and commercial ability of the resulting toothbrush. Moreover, by utilizing relatively short length bristles for the movable bristles, and longer bristles for the stationary bristles, a greater proportion of the brushing load is assumed by the stationary bristles. This generally further reduces power demands on the motor and drive mechanism of the toothbrush.

As noted, the various reciprocating bristle holders described herein may also utilize a drive mechanism that provides a shaft that rotates. Furthermore, it will be appreciated that other motor and reciprocating or rotating shaft arrangements can be substituted. For example, U.S. Pat. Nos. 5,226,206; 5,524,312; 5,383,242; 5,465,444; 5,504,959; 5,836,030; 4,845,795; 5,404,608; 5,359,747; and 5,617,601, disclose other motor and reciprocating shaft arrangements that might be suitable. In addition, the electric toothbrush described herein might be provided with a replaceable head. A suitable arrangement which can be adapted to the present invention is disclosed in U.S. application Ser. No. 09/850,662, filed May 7, 2001. Similarly, the drive mechanisms disclosed in U.S. applications Ser. Nos. 10/114,780 filed Apr. 3, 2002; and 10/128,018 filed Apr. 22, 2002, both of which are herein incorporated by reference, are also contemplated for use in conjunction with the present invention. Furthermore, U.S. published patent application No. 2003/0226223, Ser. No. 10/274,700 filed on Oct. 21, 2002, is hereby incorporated by reference.

The present invention has been described with reference to particular embodiments. Modifications and alterations will occur to others upon reading and understanding this specification. Furthermore, although certain arrangements for the fixed and movable bristles and various drive mechanisms have been shown and described, the present invention includes a variety of other configurations. It is intended that all such modifications and alterations are included insofar as they come within the scope of the appended claims or equivalents thereof.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An electric toothbrush comprising:
   a handle defining a hollow interior region with a motor disposed therein;
   a head comprising a movable bristle holder, wherein said movable bristle holder has bristles disposed thereon;
   a neck extending between said handle and said head; and
   a drive shaft defining a longitudinal axis, wherein said drive shaft extends through said neck and operatively connects said motor to said movable bristle holder for transferring power from said motor to said movable bristle holder, wherein upon operation of said motor, said drive shaft undergoes reciprocating motion, and wherein said drive shaft comprises at least one spring element integrally formed with said drive shaft between said motor and said movable bristle holder, said at least one spring element being substantially rigid and unchanged in shape when said drive shaft adjacent said movable bristle holder is not excessively loaded to transfer power from said motor to said drive shaft adjacent said movable bristle holder without any significant loss in efficiency and relatively flexible upon application of an excessive load to said drive shaft adjacent said movable bristle holder which limits movement thereof so that said motor causes said at least one spring element to undergo repeated displacements by absorbing at least some of the power from said motor which enables said motor to continue to operate while consuming ordinary levels of power even though said drive shaft adjacent said movable bristle holder is excessively loaded and has its movement limited.

2. The electric toothbrush of claim 1, wherein said at least one spring element and said drive shaft are formed from the same material.

3. The electric toothbrush of claim 1, wherein said at least one spring element and said drive shaft are formed from different materials.

4. The electric toothbrush of claim 1, wherein said at least one spring element is a linear spring.

5. The electric toothbrush of claim 1, wherein said at least one spring element comprises a first spring element and a second spring element.

6. The electric toothbrush of claim 5, wherein said second spring element exhibits a spring constant different than a spring constant of said first spring element.

7. The electric toothbrush of claim 5, wherein said first spring element is formed from a material different than that forming said second spring element.

8. The electric toothbrush of claim 1, wherein the excessive load is a load which would result in substantial stalling of said motor if said at least one spring element was not present on said drive shaft.

9. The electric toothbrush of claim 8, wherein said substantial stalling of said motor results in a reduction in the rate of movement of said movable bristle holder by about 50 percent to less than about 100 percent.

10. The electric toothbrush of claim 9, wherein the reduction in the rate of movement of said movable bristle holder is about 75 percent to 95 percent.

11. The electric toothbrush of claim 8, wherein the movable bristle holder is mounted for relative movement on said head.

12. The electric toothbrush of claim 1, wherein the movable bristle holder is mounted for relative movement on said head.

* * * * *